United States Patent
Neumann et al.

(10) Patent No.: US 9,452,970 B2
(45) Date of Patent: Sep. 27, 2016

(54) METHOD FOR HYDROGENATING NITROAROMATIC SYSTEMS WITH SELECTED PLATINUM CATALYSTS

(71) Applicant: Allessa GmbH, Frankfurt (DE)

(72) Inventors: Doris Neumann, Offenbach (DE); Joachim Ritzer, Rosenbach (DE)

(73) Assignee: ALLESSA GMBH, Frankfurt (DE)

( * ) Notice: Subject to any disclaimer, the term of this patent is extended or adjusted under 35 U.S.C. 154(b) by 0 days.

(21) Appl. No.: 14/016,317

(22) Filed: Sep. 3, 2013

(65) Prior Publication Data
US 2014/0066658 A1    Mar. 6, 2014

(30) Foreign Application Priority Data

Sep. 6, 2012  (EP) .................................... 12006277

(51) Int. Cl.
| | | |
|---|---|---|
| *C07C 209/36* | (2006.01) | |
| *B01J 27/188* | (2006.01) | |
| *B01J 21/18* | (2006.01) | |
| *B01J 23/42* | (2006.01) | |
| *B01J 37/02* | (2006.01) | |

(52) U.S. Cl.
CPC .......... *C07C 209/365* (2013.01); *B01J 27/188* (2013.01); *B01J 21/18* (2013.01); *B01J 23/42* (2013.01); *B01J 37/0201* (2013.01); *Y02P 20/52* (2015.11)

(58) Field of Classification Search
CPC .................................................. C07C 209/365
See application file for complete search history.

(56) References Cited

U.S. PATENT DOCUMENTS 3,265,636 A * 8/1966 Spiegler ........................ 502/185

FOREIGN PATENT DOCUMENTS

| | | |
|---|---|---|
| DE | 3537247 A1 | 4/1987 |
| EP | 0 842 920 A2 | 5/1998 |
| WO | 96/36597 A1 | 11/1996 |
| WO | 2011/036479 A2 | 3/2011 |

OTHER PUBLICATIONS

P. Baumeister, H.-U. Blaser and M. Studer, "Strong Reduction of Hydroxylamine Accumulation in the Catalytic Hydrogenation of Nitroarenes by Vanadium Promoters", Catalysis Letters 1997, 49, pp. 219-222.
U. Siegrist, P. Baumeister, H.-U. Blaser and M. Studer, "The Selective Hydrogenation of Functionalized Nitroarenes: New Catalytic Systems", Chemical Industries (Dekker), 1998, 75 (Catalysis of Organic Reactions), pp. 207-219.
B. Zhao, C.-J. Chou and Y.-W. Chen, "Hydrogenation of p-Chloronitrobenzene on Tungsten-Modified NiCoB Catalyst", Industrial & Engineering Chemistry Research 2010, 4, pp. 1669-1676.
A. Maltha, S.C. van Wermeskerken, B. Brunet, V. Ponec, "Transition Metal Oxides as Catalysts for the Selective Reduction of Nitrobenzene", Journal of Molecular Catalysis 93 (1994), pp. 305-316.
Z. Chen, F. Zhao, C. Ma, Y. Huang, J. Sheng, "Preparation and nitrobenzene electro-reduction performance of tungsten carbide supported platinum catalysts" (Abstract only as provided by Chemical Abstracts Service, Columbus OH), Huagong Xuebao (Chinese Edition) (2008), 59 (51), 75-79.

* cited by examiner

*Primary Examiner* — Clinton Brooks
(74) *Attorney, Agent, or Firm* — Michael W. Ferrell

(57) ABSTRACT

A method is described for the catalytic hydrogenation of aromatic nitro compounds with hydrogen to the corresponding amines in the presence of a supported catalyst comprising platinum. The method is characterized in that the catalyst comprising platinum has been modified with a tungsten compound and with a phosphorus compound in an oxidation state of <5. High yields and high selectivities are possible with the method.

14 Claims, No Drawings

METHOD FOR HYDROGENATING NITROAROMATIC SYSTEMS WITH SELECTED PLATINUM CATALYSTS

CLAIM FOR PRIORITY

This application is based on European Patent Application No. EP 12006277.3, entitled "Verfahren zur Hydrierung von Nitroaromaten mit ausgewählten Platinkatalysatoren", filed Sep. 6, 2012. The priority of European Patent Application No. EP 12006277.3 is hereby claimed and its disclosure incorporated herein by reference in its entirety.

TECHNICAL FIELD

The present invention relates to a method for the catalytic hydrogenation of aromatic nitro compounds to the corresponding aromatic amino compounds over platinum catalysts modified with tungsten in the presence of phosphorus compounds.

BACKGROUND

The hydrogenation of aromatic nitro compounds over noble metal catalysts, such as Pd/C or Pt/C, is an important synthetic route to the corresponding aromatic amino compounds. However, the course of this reaction via a series of intermediates can be problematic. Hydroxylamines, which are formed as intermediates and which in the ideal course of a hydrogenation immediately react further, may accumulate in the reaction mixture with less active or unsuitable catalysts. Hydroxylamines are generally thermally unstable. The reaction mixture may therefore suddenly exothermically decompose. Moreover, undesired by-products are often formed starting from hydroxylamines. Furthermore, other groups present in the molecule, such as halogen substituents, may also be hydrogenated or cleaved off during the reaction with hydrogen and thus further undesired by-products may be formed.

It is known from the literature that an accumulation of unstable intermediates during the hydrogenation of nitro aromatic systems can be minimized by modification of noble metal catalysts with vanadium and phosphorus compounds in an oxidation state of <5. M. Studer and P. Baumeister in WO-A-96/36597 and P. Baumeister, H.-U. Blaser and M. Studer in Catalysis Letters 1997, 49, 219-222 thus describe the treatment of noble metal catalysts with various metals and state that treatment with vanadium compounds in particular is successful.

U. Siegrist, P. Baumeister, H.-U. Blaser and M. Studer in Chemical Industries (Dekker), 1998, 75 (Catalysis of Organic Reactions), 207-219 and P. Baumeister, U. Siegrist and M. Studer in EP-A-842920 describe an additional positive effect of phosphorus compounds in an oxidation state of <5.

Aufdenblatten, Rhony, Belser and Quittmann describe in WO-A-2011/036479 a process for the catalytic hydrogenation of aromatic or heteroaromatic nitro compounds to the corresponding amines over platinum catalysts, which were modified with a molybdenum and phosphorus compound in an oxidation state of <5.

Zhao, Chou and Chen describe in Industrial & Engineering Chemistry Research 2010, 49(4), 1669-1676 the use of W-modified Ni—Co—B catalysts for hydrogenating p-chloronitrobenzene, but not the use of platinum catalysts for hydrogenation.

Becher, Birkenstock, Waldau, Witt describe in DE-A-35 37 247 the use of modified Raney nickel catalysts for hydrogenating aromatic dinitro compounds to diamino compounds. Modifying metals used in this connection are, inter alia, Fe, Cr, Cu, Mo, Ta, W, V, Ti, Nb, Re, Ru, Zr, Hf. Platinum is also not used here.

SUMMARY OF INVENTION

It has now been found, surprisingly, that platinum catalysts modified with tungsten compounds in the presence of phosphorus compounds in an oxidation state of <5 can be used advantageously for hydrogenating optionally substituted nitroaromatic systems.

The object of the present invention is to provide a hydrogenation method which has short reaction times and which affords a high space time yield. Moreover, the method according to the invention is notable for the fact that the unstable intermediates are rapidly processed and are further hydrogenated to the amines. By-products based on these unstable intermediates are undetectable or detectable only in traces in the product. Furthermore, halogen cleavage, for example, is very low for the hydrogenation of halogen-substituted nitroaromatic systems.

This effect is all the more surprising when the properties of the further elements of the $6^{th}$ transition group are considered. If a Pt/C catalyst is doped with chromium and this is used for hydrogenating halonitroaromatic systems, then, although the dehalogenation is decreased compared to hydrogenating over a nondoped catalyst, it is still in the single-digit percentage range (see comparative example 4).

The hydrogenation over a Pt/C catalyst doped with molybdenum and hypophosphorous acid affords a hydrogenation solution comprising amounts of dehalogenation products comparable to those of a Pt/C catalyst doped with chromium (see comparative example 5).

In contrast, if tungsten is used for doping a Pt/C catalyst, then hydrogenation mixtures are obtained which very suprisingly comprise considerably lower amounts of dehalogenation products, these accounting for only <0.1.

The present invention relates to a method for the catalytic hydrogenation of aromatic nitro compounds with hydrogen to the corresponding amines in the presence of a supported catalyst comprising platinum. The method is characterized in that the catalyst comprising platinum has been modified with a tungsten compound and with a phosphorus compound in an oxidation state of <5.

Other aspects and advantages of the present invention are described in the detailed description below and in the claims.

DETAILED DESCRIPTION

The invention is described in detail below with reference to several embodiments and numerous examples. Such discussion is for purposes of illustration only. Modifications to particular examples within the spirit and scope of the present invention, set forth in the appended claims, will be readily apparent to one of skill in the art. Terminology used herein is given its ordinary meaning consistent with the exemplary definitions set forth immediately below.

Any carbocyclic aromatic or heterocyclic aromatic compounds having at least one aromatic ring and at least one nitro group bonded covalently to it can be used as aromatic nitro compounds in the method according to the invention.

The aromatic nitro compounds can be monocyclic or polycyclic carbocyclic aromatic nitro compounds, preferably tricyclic, bicyclic or particularly monocyclic carbocyclic aromatic nitro compounds; or they can be monocylic or polycyclic heterocyclic aromatic nitro compounds, preferably having one or two ring heteroatoms selected from the group consisting of nitrogen, oxygen and sulfur or combinations thereof.

These carbocyclic or heterocyclic aromatic compounds have at least one nitro group, and optionally one or more substituents, for example substituents selected from the group consisting of alkyl, alkoxy, hydroxyalkyl, cycloalkyl, cycloalkoxy, aryl, aryloxy, aralkyl, aralkyloxy, carboxylic acid, sulfonic acid, amino, carboxylic ester, carboxamide, sulfonic ester, sulfonamide and/or nitrile groups and/or halogen atoms or combinations of two or more of these groups or atoms.

Preference is given to using carbocyclic or heterocyclic aromatic compounds having one to three nitro groups.

Particular preference is given to using carbocyclic or heterocyclic aromatic compounds having one to three nitro groups which have no further substituents.

Particular preference is also given to using carbocyclic or heterocyclic aromatic compounds having one to three nitro groups which have one to three halogen atoms as further substituents, particularly chlorine or bromine atoms.

Examples of alkyl groups are straight-chain or branched alkyl groups having one to sixteen carbon atoms, such as methyl, ethyl, propyl, isopropyl, n-butyl, sec-butyl, tert-butyl, pentyl, n-hexyl, n-heptyl, 2-ethylhexyl, n-octyl, n-nonyl or n-decyl, n-undecyl, n-dodecyl, n-tridecyl, n-tetradecyl, n-pentadecyl or n-hexadecyl.

Examples of alkoxy groups are those having straight-chain or branched alkyl groups having one to sixteen carbon atoms, such as methoxy, ethoxy, isopropoxy, n-butoxy, sec-butoxy, tert-butoxy, pentyloxy, n-hexyloxy, n-heptyloxy, 2-ethylhexyloxy, n-octyloxy, n-nonyloxy, n-decyloxy, n-tridecyloxy, n-tetradecyloxy, n-pentadecyloxy or n-hexadecyloxy.

Examples of cycloalkyl groups are those having five or six ring carbon atoms, which in turn may be substituted, for example with alkyl groups. An example of a cycloalkyl group is cyclohexyl.

Examples of cycloalkoxy groups are those having five or six ring carbon atoms in the cycloalkyl ring, which in turn may be substituted, for example with alkyl groups. An example of a cycloalkoxy group is cyclohexyloxy.

Examples of aryl groups are those having six or ten ring carbon atoms in the aryl ring, which in turn may be substituted, for example with alkyl groups. An example of an aryl group is phenyl.

An example of an aralkyl group is benzyl, which in turn may be substituted, for example with alkyl groups.

An example of a carboxamide group is $C_1$-$C_4$-acylamino, preferably acetylamino.

The carbocyclic or heterocyclic aromatic nitro compounds may have, in addition to aromatic rings, further nonaromatic saturated or ethylenically unsaturated rings which are fused with the aromatic rings or are linked to the aromatic rings via covalent bonds or form a bicyclic or polycyclic system with the aromatic rings.

Examples of aromatic nitro compounds used with particular preference are those which are derived from phenyl groups, substituted phenyl groups, naphthyl groups, substituted naphthyl groups, anthracenyl groups and substituted anthracenyl groups and which have one or two nitro groups and optionally one to three chlorine or bromine atoms.

In the context of this description, halogen is fluorine, chlorine, bromine or iodine. Preference is given to chlorine and bromine and very particular preference to chlorine.

Particular preference is given to using aromatic nitro compounds of the general structural formula I or II

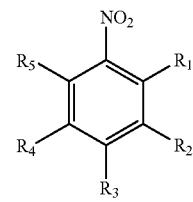

(I)

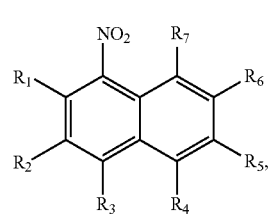

(II)

where $R_1$, $R_2$, $R_3$, $R_4$, $R_5$, $R_6$ and $R_7$ are each independently hydrogen, halogen, alkyl, which may in turn be substituted at one or more carbon atoms with halogen groups or with groups containing oxygen or nitrogen, or in which one or more nonadjacent carbon atoms have been replaced by oxygen, nitrogen or sulfur atoms, or are further nitro groups, and wherein optionally one to three ring carbon atoms in the compounds of the formula I or II are replaced by nitrogen, oxygen and/or sulfur atoms.

Groups containing oxygen include, for example, alkoxy, cycloalkyloxy, aryloxy, carboxyl or carboxylic ester groups.

Groups containing nitrogen include, for example, N-alkylamino, N,N-dialkylamino, N-cycloalkylamino, N,N-dicycloalkylamino, N-arylamino, N,N-diarylamino, amino or amide groups.

The alkyl groups in which one or more nonadjacent carbon atoms have been replaced by oxygen, nitrogen or sulfur atoms include, for example, monofunctional polyalkylene glycol residues, for example polyethylene glycol residues, or the corresponding sulfur or amino homologs.

The aromatic nitro compounds are hydrogenated with high selectivity to the corresponding aromatic amines by the method according to the invention.

In the formulae I and II, $R_1$, $R_2$, $R_3$, $R_4$, $R_5$, $R_6$ and $R_7$ are preferably, independently of each other, hydrogen, $C_1$-$C_6$-alkyl, $C_1$-$C_6$-alkoxy, $C_1$-$C_4$-acylamino or halogen, wherein 1 to 4 of the residues $R_1$ to $R_7$ are particularly preferably different from hydrogen.

With particular preference, in the compounds of the formula I, two to five of the substituents $R_1$ to $R_5$ are hydrogen and zero to three of the substituents $R_1$ to $R_5$ are halogen, particularly chlorine or bromine.

With particular preference, in the compounds of the formula I, one to two of the substituents $R_1$ to $R_5$ are nitro, zero to four of the substituents $R_1$ to $R_5$ are hydrogen and zero to three of the substituents $R_1$ to $R_5$ are halogen, particularly chlorine or bromine.

With particular preference, in the compounds of the formula II, three to seven of the substituents $R_1$ to $R_7$ are hydrogen and zero to four of the substituents $R_1$ to $R_7$ are halogen, particularly chlorine or bromine.

With particular preference, in the compounds of the formula II, one to two of the substituents $R_1$ to $R_7$ are nitro, one to six of the substituents $R_1$ to $R_7$ are hydrogen and zero to four of the substituents $R_1$ to $R_7$ are halogen, particularly chlorine or bromine.

The hydrogenations are carried out in solution. Suitable solvents are water, hydrocarbons, for example linear, branched or cylic $C_1$-$C_{12}$-alkanes, unsubstituted or substituted with halogen, oxygen or nitrogen, and also monocyclic or polycyclic $C_6$-$C_{16}$-aryl or heteroaryl compounds, unsubstituted or substituted with halogen, oxygen or nitrogen, or alcohols, for example linear or branched monohydric or polyhydric $C_1$-$C_{10}$-alcohols, or ethers, for example ethers derived from linear or branched monohydric or polyhydric $C_1$-$C_{10}$-alcohols, or carboxylic esters, for example esters derived from linear or branched monohydric or polyhydric $C_1$-$C_{10}$-alcohols with $C_1$-$C_4$-carboxylic acids or mixtures of said solvents or of said solvents with water.

The solvents preferably used are water, hexane, heptane, octane, cyclohexane, toluene, o-, m- and p-xylene, phenol, o-, m- and p-cresol, anisole, chlorobenzene, dichlorobenzene, methanol, ethanol, n- or isopropanol, n-, sec- or tert-butanol, 2-pentanol, 3-pentanol, 2-methylbutan-2-ol, 2-methylpentan-2-ol, 2-methylpentan-3-ol, 3-methylpentan-2-ol, 4-methylpentan-2-ol, 2,3-dimethyl-2-butanol, 3,3-dimethyl-2-butanol.

Particular preference is giving to using heptane, octane, cyclohexane, toluene, o-, m- and p-xylene, phenol, o-, m- and p-cresol, anisole, chlorobenzene, methanol, ethanol, n- or isopropanol, n-, sec or tert-butanol, 2-pentanol, 3-pentanol, 2-methylbutan-2-ol, 2-methylpentan-2-ol, 2-methylpentan-3-ol, 3-methylpentan-2-ol, 4-methylpentan-2-ol, diethyl ether, diisopropyl ether, diphenyl ether, methyl acetate, ethyl acetate, n- and isopropyl acetate, acetic acid n-, sec- or tert-butyl ester.

The concentration of the aromatic nitro compound in the solvent is selected to be between 10 and 90%, preferably 20 and 80%, particularly preferably 30 and 70%.

In the case of liquid aromatic nitro compounds, these can also act as solvent at the same time.

The platinum catalysts used can be commercially available supported catalysts comprising platinum. The platinum content of these catalysts is typically 0.3-10% by weight of platinum, preferably 0.3-8% by weight of platinum, particularly preferably 0.5-5% by weight of platinum. Here, the percentages are based on the dry weight of the supported catalyst.

A wide variety of materials are suitable as supports. Examples of these are aluminum oxide, ceramic support materials or carbon or graphite, for example activated charcoal. Support materials for these catalysts are known to those skilled in the art and are generally used in finely divided form, which may optionally be compacted into pellets. Particular preference is given to using carbon, particularly activated charcoal, as support material. The catalysts may be used as solids, e.g. as powders or pellets, but also as commercially available water-moist pastes.

The catalytically active metal is platinum or a combination of platinum with other metals, for example with palladium or rhodium.

The catalyst may be doped with other components in addition to the catalytically active metal, for example with alkali metals or alkaline earth metals and/or with rare earth metals.

Very particular preference is given to using a platinum catalyst supported on carbon (hereinafter "Pt/C catalyst"). Any desired carbon support may be used. These Pt/C catalysts are commercially available.

The molar amount of platinum used, based on the nitro component, is generally between $1*10^{-7}$ and $1*10^{-2}$ mole equivalents, preferably between $1*10^{-6}$ and $5*10^{-3}$ mole equivalents and particularly preferably between $5*10^{-6}$ and $1*10^{-3}$ mole equivalents.

The catalyst is present suspended in the reaction mixture and the aromatic nitro compound is dissolved in the solvent or is already present in liquid form and forms a liquid phase which reacts with the hydrogen present in the gas phase.

The aromatic nitro compound may also be added as such or as a solution to the charged catalyst, which has been slurried in the whole amount or a portion of the solvent, in parallel to the metering in of hydrogen.

Suitable tungsten compounds used are those in an oxidation state of 4 or 6, e.g. oxides, halides or oxychlorides, tungstic acid or a salt thereof.

Preference is given to using tungsten(IV) or tungsten(VI) oxide, tungsten(VI) oxychloride, tungsten hexachloride, tungstic acid or an alkali metal or alkaline earth metal salt thereof, particularly preferably tungstic acid, or tungstates of lithium, sodium, potassium, magnesium or calcium.

The molar ratio of platinum:tungsten is generally selected to be between 20:1 and 1:20, preferably between 15:1 and 1:15, particularly preferably between 8:1 and 1:8, very particularly preferably from 5:1 to 1:5, especially preferably from 4:1 to 1:4, and most preferably from 3:1 to 1:3.

The phosphorus compound used in an oxidation state of <5 is preferably selected from the group consisting of the phosphines $PR_{3-n}H_n$, the phosphinic acids $P(OH)R_{2-m}H_m$, the phosphine oxides $P(O)R_{3-n}H_n$, the hypophosphorous acids $P(OH)(O)R_{2-m}H_m$ and the phosphorous acids $P(OH)_2(O)H$ or $P(OH)_2(O)R$, in which R is an organic residue, particularly a linear or branched $C_1$-$C_{14}$ alkyl residue or a $C_6$-$C_{16}$ aryl residue, n=0-3 and m=0-2, and also from the salts, esters or anhydrides of the phosphorus compounds mentioned.

For this purpose, preference is given to using propanephosphonic acid, propanephosphonic anhydride, phosphorous or hypophosphorous acid or a salt, particularly an alkali metal salt or alkaline earth metal salt of these acids, with particular preference given to phosphorous or hypophosphorous acid or a salt, particularly an alkali metal salt or alkaline earth metal salt of these acids.

The proportion of the phosphorus compound, based on the aromatic nitro compound, is generally selected to be between $1*10^{-6}$ and $1*10^{-1}$ mole equivalents, preferably between $1*10^{-5}$ and $5*10^{-2}$ mole equivalents, particularly preferably between $1*10^{-4}$ and $1*10^{-3}$ mole equivalents.

The platinum catalyst used in the method according to the invention, before being used with the tungsten compound and with the phosphorus compound, is generally treated with a solution of these compounds, or the tungsten compound and the phosphorus compound are added to the hydrogenation mixture. In the latter case, it is also possible to use previously untreated supported platinum catalysts. The tungsten compound and the phosphorus compound may be added to the supported catalyst without solvent or preferably as a solution in a suitable solvent, particularly as an aqueous solution. Mixtures of tungsten compounds and/or phosphorus compounds may also be used.

The method described may be carried out in any reactors. Preferred examples of these are stirred or loop reactors.

The hydrogenation times of the method described are generally between one and three hours. In individual cases, however, shorter or longer reaction times can also be used.

On carrying out the method according to the invention, it has been found that good yields and selectivities of aromatic amino compounds are generally obtained at temperatures of 50 to 250° C., preferably 60 to 250° C., particularly preferably 60 to 200° C. and very particularly preferably 70 to 180° C.

The method according to the invention can be carried out at various hydrogen pressures. The selectivity and the reaction conversion are the maximum at a hydrogen pressure of 0.5-60 bar. Hydrogenation is preferably carried out at 0.5-50 bar, particularly preferably at 1-40 bar.

The advantages of the method according to the invention are a high yield and a high selectivity.

A further advantage of the method according to the invention is the feasibility of the method in the presence of water. By removing the complex drying steps, the productivity of the method is considerably increased.

An additional advantage of the method according to the invention is the reusability of the catalysts. The costs of the catalysts can thereby be distinctly reduced.

The following examples illustrate the invention but are not limited to these.

EXAMPLE 1

103 g of o-chloronitrobenzene were dissolved in 304 g of toluene and placed in an autoclave. 0.4 g of a commercial Pt/C catalyst (5% Pt/C, 50% water moisture) was suspended in water, admixed with 0.7 g of a 1% sodium tungstate solution and 0.9 g of 5% hypophosphorous acid and added to the chloronitrobenzene solution in the autoclave. The autoclave was heated to 90° C. and 20 bar hydrogen was applied. The hydrogenation was continued until the hydrogen uptake ceased. The hydrogenation solution comprised 99.5% o-chloroaniline in addition to only 0.04% aniline (dehalogenation product).

EXAMPLE 2

101 g of p-chloronitrobenzene were dissolved in 300 g of toluene and the solution placed in an autoclave. 0.5 g of a commercial Pt/C catalyst (5% Pt/C, 50% water moisture) were suspended in water, admixed with 0.8 g of a 1% sodium tungstate solution and 0.9 g of 5% hypophosphorous acid and added to the chloronitrobenzene solution in the autoclave. The autoclave was heated to 95° C. and 20 bar hydrogen was applied. The hydrogenation was continued until the hydrogen uptake ceased. The hydrogenation solution comprised 99.5% p-chloroaniline in addition to only 0.01% aniline (dehalogenation product).

COMPARATIVE EXAMPLE 1

Doped Catalyst without Hypophosphorous Acid 105 g of o-chloronitrobenzene were dissolved in 304 g of toluene. 0.4 g of a commercial Pt/C catalyst (5% Pt/C, 50% water moisture) were suspended in water, admixed with 0.65 g of a 1% sodium tungstate solution and placed in the autoclave together with the chloronitrobenzene solution. Hydrogenation was carried out at 90-100° C. and 20 bar hydrogen pressure until the hydrogen uptake ceased.

The hydrogenation solution comprised 81.7% o-chloroaniline in addition to 6.5% aniline (dehalogenation product) and further unknowns.

COMPARATIVE EXAMPLE 2

Undoped Catalyst without Hypophosphorous Acid 101 g of o-chloronitrobenzene were dissolved in 301 g of toluene. 0.4 g of a commercial Pt/C catalyst (5% Pt/C, 50% water moisture) were suspended in water and placed in the autoclave together with the chloronitrobenzene solution. Hydrogenation was carried out at 90 to 110° C. and 20 bar hydrogen pressure until the hydrogen uptake ceased. The hydrogenation solution comprised only 87.6% o-chloroaniline in addition to 5.2% aniline (dehalogenation product) and further unknowns.

COMPARATIVE EXAMPLE 3

Undoped Catalyst with Hypophosphorous Acid 103 g of o-chloronitrobenzene were dissolved in 301 g of toluene and placed in an autoclave. 0.4 g of a commercial Pt/C catalyst (5% Pt/C, 50% water moisture) were suspended in water, admixed with 0.9 g of 5% hypophosphorous acid and added to the chloronitrobenzene solution in the autoclave. The autoclave was heated to 90° C. and 20 bar hydrogen was applied. The hydrogen uptake ceased before the theoretically calculated amount had been taken up. Analysis of the reaction solution showed that a series of unknowns was present in addition to nonhydrogenated reactant and o-chloroaniline.

COMPARATIVE EXAMPLE 4

Pt/C Catalyst Doped with Chromium

A solution of 100 g of o-chloronitrobenzene in 400 g of toluene was hydrogenated over a commercial Pt/C catalyst, which had been pretreated with 0.2 g of a 1% aqueous chromium trioxide solution, at 100° C. and 20 bar hydrogen pressure. The hydrogenation time was 3 h. The hydrogenation mixture comprised 98.1% o-chloroaniline in addition to 1.5% aniline and minor amounts of further by-products.

COMPARATIVE EXAMPLE 5

Pt/C Catalyst Doped with Molybdenum 100 g of o-chloronitrobenzene were dissolved in 400 g of toluene and hydrogenated at 100° C. and 20 bar hydrogen pressure over 0.4 g of a commercial Pt/C catalyst which had been pretreated with 4.4 g of a 1% aqueous ammonium heptamolybdate solution. After a hydrogenation time of 1 h, the hydrogenation mixture comprised 99.0% o-chloroaniline in addition to 1.0% aniline.

Additional Embodiments

In general, the invention provides a method for the catalytic hydrogenation of aromatic nitro compounds with hydrogen, in the presence of a supported catalyst comprising platinum, to the corresponding amines. The catalyst is modified with a tungsten compound and with a phosphorus compound in an oxidation state of <5. The foregoing method may be operated with the following alternative parameters.

The aromatic nitro compound may be substituted with substituents such as halogen atoms. The concentration of the aromatic nitro compound in solvent is generally 10-90% by weight, preferably 20-80% by weight, particularly preferably 30-70% by weight.

The catalysts may be powders or pellets or may be water-moist pastes.

The catalyst may have a platinum content of 0.3-10% by weight, such as 0.3-8% by weight of platinum, preferably 0.5-5% by weight of platinum. The molar amount of platinum used, based on the nitro content, may be between $1 \times 10^{-7}$ and $1 \times 10^{-2}$ mole equivalents, such as between $1\times10^{-6}$ and $5\times10^{-3}$ mole equivalents and preferably between $5\times10^{-6}$ and $1\times10^{-3}$ mole equivalents.

The tungsten compounds used may be tungstates of lithium, sodium, potassium, magnesium or calcium. Further, the tungsten compound used may be an oxide, halide or oxychloride, tungstic acid or a salt thereof.

The molar ratio of platinum:tungsten is generally between 20:1 and 1:20 and may be between 15:1 and 1:15, preferably between 8:1 and 1:8, particularly preferably from 5:1 to 1:5, especially preferably from 4:1 to 1:4, and most preferably from 3:1 to 1:3.

The proportion of the phosphorus compound, based on the aromatic nitro compound, is generally between $1\times10^{-6}$ and $1\times10^{-1}$, preferably between $1\times10^{-6}$ and $5\times10^{-2}$ mole equivalents, particularly preferably between $1\times10^{-4}$ and $1\times10^{-3}$ mole equivalents.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. A method for the catalytic hydrogenation of aromatic nitro compounds in solution, wherein the halogenated aromatic nitro compound is a compound of the general structural formula I or II

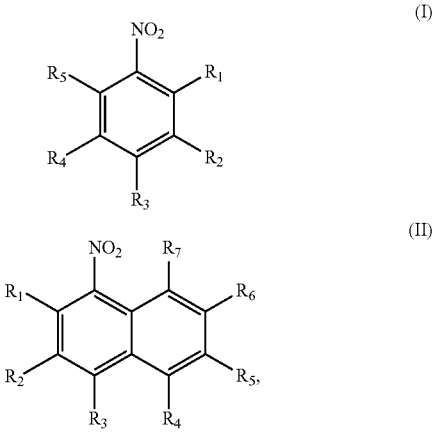

where

R$_1$, R$_2$, R$_3$, R$_4$, R$_5$, R$_6$ and R$_7$ are each independently hydrogen, halogen, alkyl, which may in turn be substituted at one or more carbon atoms with halogen groups or with groups containing oxygen or nitrogen, or in which one or more nonadjacent carbon atoms have been replaced by oxygen, nitrogen or sulfur atoms, or are further nitro groups, with the further proviso that at least one of R$_1$, R$_2$, R$_3$, R$_4$, R$_5$, R$_6$ or R$_7$ is a halogen atom, with hydrogen to the corresponding amines in the presence of a supported catalyst comprising platinum, wherein the catalyst comprising platinum has been modified with a tungsten compound in an oxidation state of 4 or 6 and with a phosphorus compound in an oxidation state of <5 selected from the group consisting of the phosphines $PR_{3-n}H_n$, the phosphinic acids $P(OH)R_{2-m}H_m$, the phosphine oxides $P(O)R_{3-n}H_n$, the hypophosphorous acids $P(OH)(O)R_{2-m}H_m$ and the phosphorous acids $P(OH)_2(O)H$ or $P(OH)_2(O)R$, in which R is a linear or branched $C_1$-$C_{14}$ alkyl residue or a $C_6$-$C_{16}$ aryl residue, n=0-3, m=0-2, and salts, anhydrides or esters of the phosphorus compounds mentioned.

2. The method as claimed in claim 1, wherein the aromatic nitro compound is a carbocyclic aromatic or heterocyclic aromatic, monocyclic or polycyclic compound which is substituted with at least one nitro group and which optionally may have further substituents.

3. The method as claimed in claim 1, wherein the solvents used are linear, branched or cyclic $C_1$ to $C_{12}$ alkanes, unsubstituted or substituted with halogen atoms, monocyclic or polycyclic $C_6$ to $C_{16}$ aryl or heteroaryl compounds, unsubstituted or substituted with halogen atoms or with groups containing oxygen or nitrogen or mixtures of said solvents or mixtures of said solvents with water.

4. The method as claimed in claim 1, wherein the solvents used are hexane, heptane, octane, cyclohexane, toluene, o-, m- and p-xylene, phenol, o-, m- and p-cresol, anisole, chlorobenzene, dichlorobenzene.

5. The method as claimed in claim 1, wherein the concentration of the aromatic nitro compound in the solvent is 10 to 90% by weight.

6. The method as claimed in claim 1, wherein the catalyst comprising platinum has a platinum content of 0.3-10% by weight of platinum.

7. The method as claimed in claim 1, wherein the catalyst supports used are aluminum oxide, ceramic support materials or activated charcoal.

8. The method as claimed in claim 1, wherein the catalyst used is a solid or a water-moist paste.

9. The method as claimed in claim 1, wherein the molar amount of platinum used, based on the nitro component, is between $1\times10^{-7}$ and $1\times10^{-2}$ mole equivalents.

10. The method as claimed in claim 1, wherein the tungsten compounds used are tungsten(IV) or tungsten(VI) oxide, tungsten(VI) oxychloride, tungsten hexachloride, tungstic acid or an alkali metal or alkaline earth metal salt thereof.

11. The method as claimed in claim 1, wherein the molar ratio of platinum : tungsten is between 20:1 and 1:20.

12. The method as claimed in claim 1, wherein the phosphorus compound used is propanephosphonic acid, phosphorous or hypophosphorous acid or a salt, anhydride or ester of these acids.

13. The method as claimed in claim 1, wherein the proportion of the phosphorus compound, based on the aromatic nitro compound, is between $1\times10^{-6}$ and $1\times10^{-1}$ mole equivalents.

14. The method as claimed in claim 1, wherein the carbon support used is activated charcoal.

* * * * *